United States Patent [19]

Hagert

[11] 4,150,444
[45] Apr. 24, 1979

[54] PROSTHETIC JOINT

[76] Inventor: Carl-Göran A. Hagert, Barnhemsgatan 37, 43131 Mölndal, Sweden

[21] Appl. No.: 810,210

[22] Filed: Jun. 27, 1977

[30] Foreign Application Priority Data
Jun. 28, 1976 [SE] Sweden .................................. 7607345

[51] Int. Cl.² .............................................. A61F 1/24
[52] U.S. Cl. .................................... 3/1.91; 128/92 C
[58] Field of Search .............................. 3/1.9–1.912; 128/92 C

[56] References Cited
U.S. PATENT DOCUMENTS

| | | | |
|---|---|---|---|
| 3,506,982 | 4/1970 | Steffee | 3/1.91 |
| 3,795,922 | 3/1974 | Herbert et al. | 3/1.911 |
| 3,805,302 | 4/1974 | Mathys | 3/1.91 |
| 3,837,008 | 9/1974 | Bahler et al. | 3/1.91 |
| 3,896,502 | 7/1975 | Lennox | 3/1.91 |

FOREIGN PATENT DOCUMENTS

| | | | |
|---|---|---|---|
| 2531080 | 2/1976 | Fed. Rep. of Germany | 3/1.911 |
| 1333412 | 10/1973 | United Kingdom | 3/1.911 |

Primary Examiner—Ronald L. Frinks

[57] ABSTRACT

A prosthetic joint composed of a rigid joint head and a rigid socket. The joint head has a flat base face for engaging a flat surface prepared on the bone; the socket has a pair of shanks straddling the joint head. A hemispherical knob on the outer extremity of each of the shanks engages a groove in a respective one of a pair of flattened lateral faces of the joint head. One end of the groove extends to and forms an indentation into the edge of the base surface to allow insertion of the knob into the groove prior to the mounting of the joint head on the bone.

18 Claims, 22 Drawing Figures

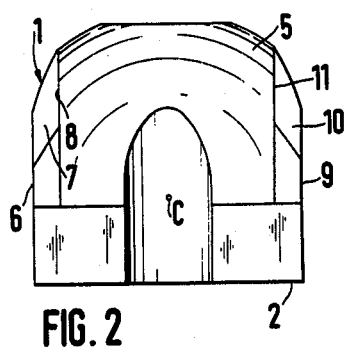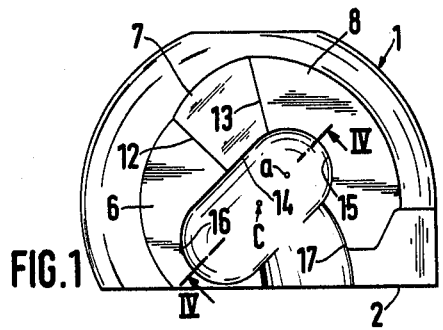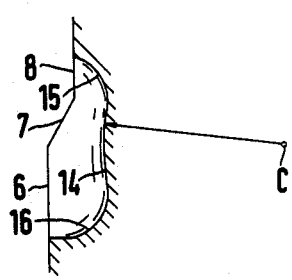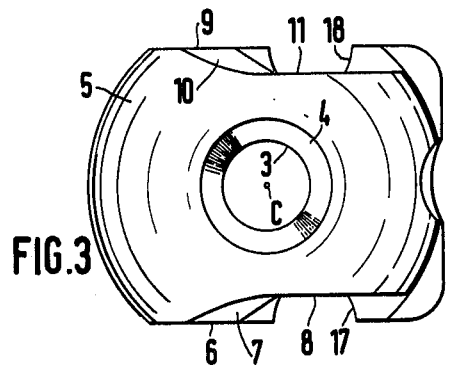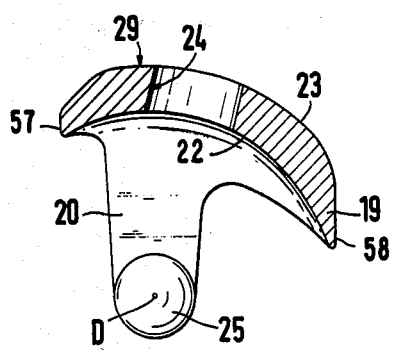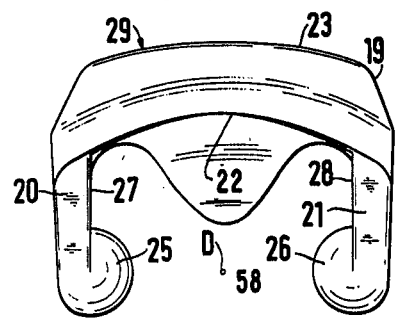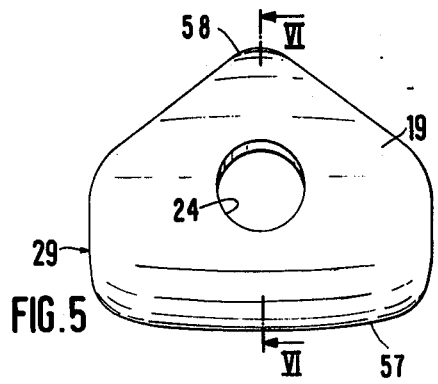

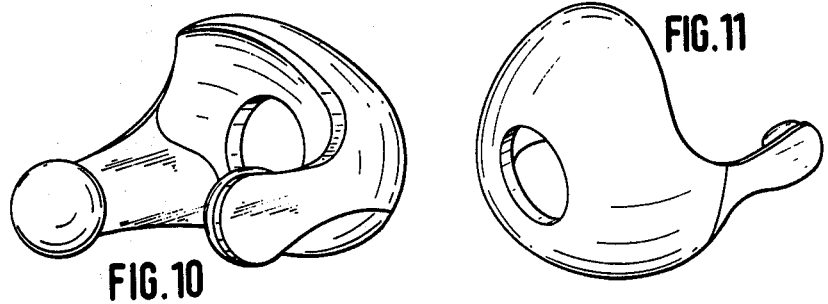
FIG. 11
FIG. 10
FIG. 8
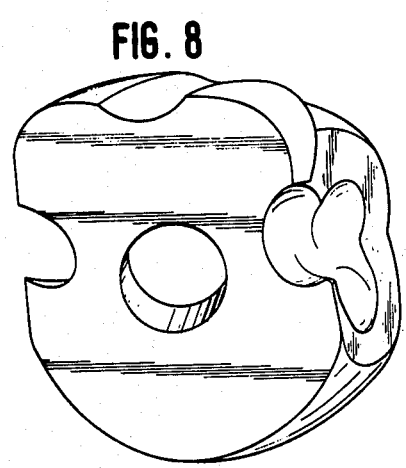
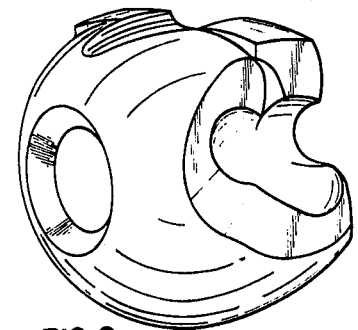
FIG. 9
FIG. 12
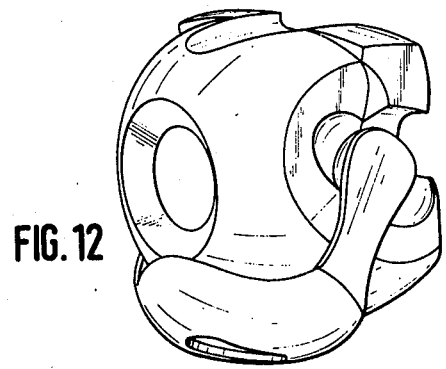

PROSTHETIC JOINT

This invention relates to prosthetic joints, more particularly to prosthetic joints of the type comprising a pair of joint members angularly movable with respect to each other.

The prior art includes many different prosthetic joints of this kind, including joints developed for the purpose of replacing finger joints rendered useless by rheumatoid arthritis. This affliction particularly attacks the metacarpophalangeal joints (usually referred to as MCP joints), that is, the joints connecting the innermost finger bones (phalanxes) to the corresponding bones of the palm (metacarpus). The clinical experiences with the prosthetic finger joints of the prior art have on the whole been disappointing. To function adequately, a prosthetic MCP joint should provide a movement pattern identical with or closely similar to the one provided by the natural MCP joint and allow amplitudes of movement of the same order as those allowed by the natural MCP joint. Also, it must have no tendency to cause bone resorption or other harmful changes or modifications of the adjoining tissues. It is also important that the fixing of the joint between the bones to be joined can be carried out quickly and simply. This applies, of course, not only to prosthetic MCP joints, but to prosthetic joints generally, including prosthetic interphalangeal joints (that is, joints between two finger bones).

The invention has for its object to provide an improved prosthetic joint, particularly an improved prosthetic MCP joint.

The prosthetic joint of the invention comprises a first and a second joint member angularly moveable with respect to each other, each of said members being arranged to be attached to one of a pair of skeletal bones. According to the invention, said first jont member is a joint head having a base face for resting on a supporting surface provided on one of the skeletal bones, a convex slide face shaped as part of a surface of revolution having an axis extending through the joint head at a distance from said base face, and a pair of opposed, flattened lateral guide faces provided each with a groove extending transversely of said base face and said axis of revolution, each of said grooves extending from an open end cutting into said base face to a closed end remote from said base face, said closed end having a spherically rounded, concave end wall, and said second joint member is a socket member comprising a bowl-shaped part having an outer top face for resting on a supporting surface provided on the other one of the pair of skeletal bones, a concave inner slide face forming part of a surface of revolution having a shape corresponding to the shape of the convex slide face of the joint head, stem portions attached to said bowl-shaped part and arranged to engage said opposed guide faces, and a pair of essentially hemispherical knobs supported by said stem portions, each of said knobs engaging one of said grooves into which it is admitted through the aforesaid open end of the groove.

A fuller understanding of the nature and the advantages of the invention will be obtained from the following description of examples of prosthetic joints according to the invention, taken in conjunction with the accompanying drawings, in which:

FIGS. 1 to 3 are views, taken at right angles to each other, of the joint head of a prosthetic MCP joint constituting a first embodiment of the invention;

FIG. 4 is a sectional view taken on the line IV—IV of FIG. 1;

FIG. 5 is an outside view of the joint socket for the joint head of FIGS. 1-4;

FIG. 6 is a sectional view taken on the line VI—VI of FIG. 5;

FIG. 7 is a view of the socket as viewed from above in FIG. 5;

FIGS. 8 and 9 are perspective drawings of a prosthetic joint head model constructed substantially according to FIGS. 1-4;

FIGS. 10 and 11 are perspective drawings of a prosthetic joint socket model constructed substantially according to FIGS. 5 to 7;

FIG. 12 is a perspective drawing of the MCP joint composed of the joint head of FIGS. 8-9 and the socket of FIGS. 10-11;

Figure 13:
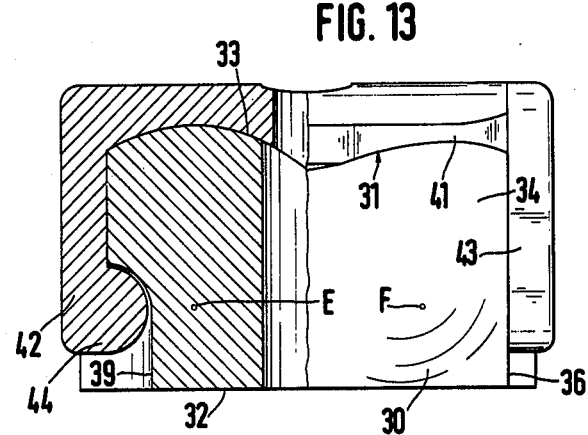
FIG. 13 is a view of a prosthetic interphalangeal joint constituting a second embodiment of the invention, certain parts being represented in sectional view taken on the line XIII—XIII in FIGS. 14 and 15.
Figure 14:
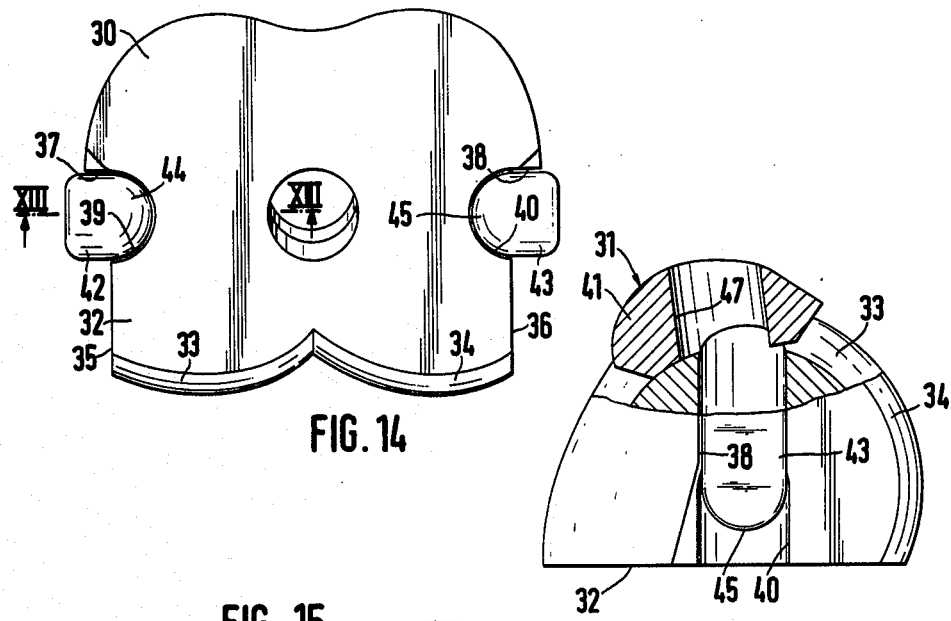
FIG. 14 is a view of the same joint taken from below in FIG. 13 (towards the flat face of the joint head)
Figure 16:
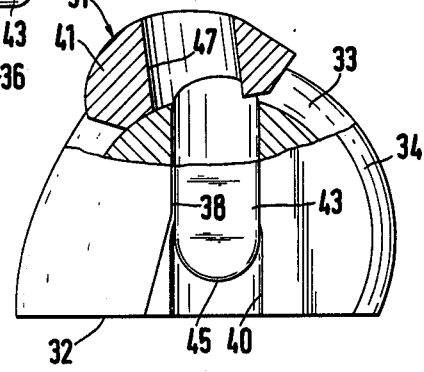
FIG. 16 is a third view, taken from the left in FIG. 15, certain parts being represented in sectional view taken on the line XVI—XVI of FIG. 15.
Figure 15:
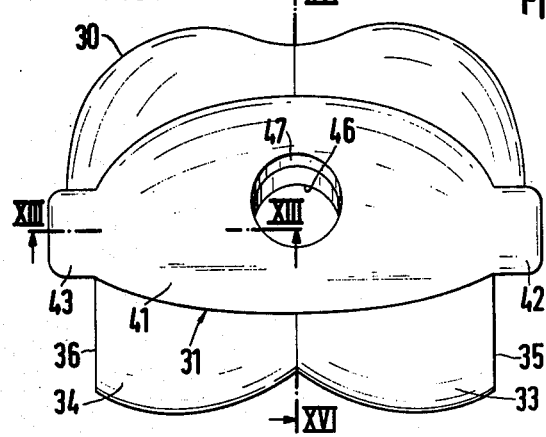
FIG. 15 is a view taken from above in FIG. 13.
Figure 17:
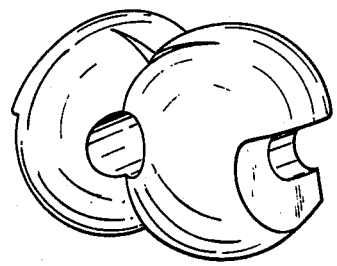
FIGS. 17 and 18 are perspective drawings of a model of a joint head for a prosthetic interphalangeal joint constructed substantially according to FIGS. 13 to 16.
Figure 19:
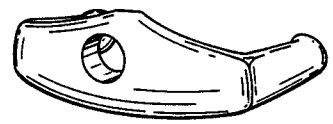
FIGS. 19 and 20 are perspective drawings of a model of a socket for a prosthetic interphalangeal joint constructed substantially according to FIGS. 13 to 16.
Figure 20:
Figure 18:
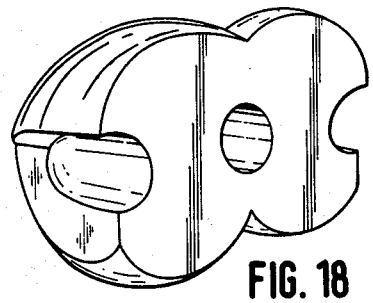
Figure 21:
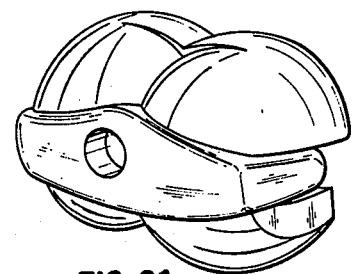
FIG. 21 is a perspective drawing of the complete prosthetic interphalangeal joint model composed of the joint head model of FIGS. 17-18 and the socket model of FIGS. 18-19.

In FIG. 1, the prosthetic joint head 1 is shown standing on its flat base face 2, the back-of-the-hand side, or knuckle side, of the joint head being turned to the right and its palm side being turned to the left in the figure. FIG. 2 shows the joint head as seen from the right in FIG. 1, that is, from the back-of-the-hand side. FIG. 3 shows the side opposite to the flat base face. The base face 2 is intended to be applied to a plane supporting surface on the metacarpal bone. The joint head is secured to the metacarpal bone by means of a screw, preferably of titanium, which is inserted into a through hole 3 in the joint head at right angles to the flat face 2 and screwed either into a bore provided in the metacarpal bone and extending in the direction of the axis of the metacarpal bone, or, preferably, into the bore of a fixture previously inserted into the metacarpal bone. Said fixture is a sleeve-shaped member, preferably of titanium, provided with exterior threads for engaging the bore in the metacarpal bone and interior threads corresponding to the threads of the screw. The end of the through hole 3 remote from the base face 2 is countersunk at 4 to receive the head of the screw. The joint head has a spherical slide face 5 the geometrical centre C of which is located on the axis of the hole 3. When the joint head has been mounted on the metacarpal bone, the centre C will therefore be located on the extension of the axis of the metacarpal bone. The joint head is provided with a pair of opposed, flattened lateral faces which are symmetrical with respect to a symmetry plane extending through the axis of the hole 3. Each of said flattened lateral faces comprises a first plane area 6, 9, respectively, a second plane area 8, 11, respectively, and a third area or sector 7, 10, respectively, forming a transition between the plane area 6, 8 and the plane area 9, 11, respectively. The planes of the areas 6, 9, 8, 11 are parallel to each other and to the symmetry plane. The distance between the areas 8 and 11 is less than the distance between the areas 6 and 9. Said last-mentioned areas are adjacent to the palm side of the joint head. In the direction away from the palm side and from the flat face 2 of the joint head, said areas are limited at least approximately by a plane extending through the centre C at right angles to the symmetry plane of the joint head and forming an angle of 45° with the flat face 2 of the joint head. Thus, the boundary line 12 (FIG. 1) between each of the plane areas 6, 9 and the adjacent one of the pair of converting sectors 7, 10 is located at least approximately in said oblique plane. The boundary 13 (FIG. 1) between each of the converting sectors 7, 10 and the adjacent one of the pair of plane areas 8, 11 is located at least approximately in a plane extending through the centre C at right angles to the symmetry plane and at least approximately at right angles to the base face 2.

Each of the flattened lateral faces of the joint head is provided with a groove 14 (FIGS. 1 and 4) having an approximately semicircular cross-sectional shape. The grooves are symmetrical with respect to each other and extend at an oblique angle to the base face 2 and the axis of the hole 3. More particularly, a plane extending through the bottom lines of both grooves forms an angle of about 45° with the flat face 2 and with the axis of the hole 3. Both of the ends of each of the grooves have a spherically rounded end wall 15, 16, respectively. The bottom line of the groove is not quite straight but slightly cambered. The camber forms a circular arc the centre of which coincides with the centre C of the spherical slide face 5 (FIG. 4). The centre a of the spherical surface of the end wall of the groove at the end remote from the flat face 2 has a distance from said flat face exceeding the distance of the centre C of the spherical slide face 5 from said flat face. The distance between the lower end wall 16 and the flat face 2 is less than the radius of the spherical surface forming the end wall.

A second, slightly curved groove 17, 18 (FIGS. 1, 3) having the same depth and the same cross-sectional shape as the groove 14 extends substantially transversely of the groove 14 from an open end at the edge of the flat face 2 to the middle portion of the groove 14. Thus, the grooves together form a tee groove the stem of which is formed by the curved portion 17 or 18 and the crosspiece of which is formed by the straight portion 14.

The other component 29 (FIGS. 5 to 7), that is the socket, of the prosthetic joint, is a U member having a yoke portion 19 and a pair of parallel shanks 20, 21. The yoke portion has the shape of a bowl the spherically rounded concave inner face of which has the same radius of curvature as the spherical surface 5 of the joint head and is intended slidably to engage said surface. The edge 57 of the bowl-shaped yoke portion which is to be adjacent to the inside (palm side) of the finger is nearly straight, with a faint curvature only (FIG. 5), while the other edge 58, which is to be adjacent to the back-of-the-hand side, or knuckle side, of the finger, forms a wedge tapering towards a rounded tip. The outside of the yoke portion has a top face 23 for engaging a supporting surface provided on the finger bone (phalanx). The yoke portion is attached to the phalanx by means of a screw inserted through a hole 24 in the yoke portion 19 and screwed into a bore provided in the phalanx in the direction of its axis (or into the bore of a fixture previously inserted into the phalanx). Each of the shanks 20, 21 is provided at its outer end with a hemispherical projection or knob 25, 26, respectively, said knobs being directed inwards towards each other and designed for sliding engagement with the grooves 14 of the joint head (cf. FIG. 12). The geometrical centre D of the spherical slide face 22 of the yoke portion 19 is located on the straight line joining the centres of the hemispherical surfaces of the knobs 25, 26 and also on the axis of the hole 24, said axis coinciding with the axis of the phalanx on which the yoke portion is mounted. The distance between the parallel insides 27, 28 of the shanks 20, 21 only slightly exceeds the distance between the plane areas 6, 9 of the lateral flattened faces of the joint head 1, so that the shanks when straddling the joint head can slide freely across said areas but are allowed no appreciable lateral play with respect to said areas.

The mounting of the prosthetic joint on the skeletal bones is carried out in the following manner. First, the socket 29 is attached to the phalanx. Next, the joint head is joined to the socket; this is done by inserting the hemispherical knobs 26, 25 of the shanks 20, 21 into the straight grooves 14 of the joint head through the transverse grooves 17, 18 and swinging the yoke portion 19 into sliding engagement with the slide face of the joint head. FIG. 12 illustrates the resulting relative positions of the joint members. Finally, the joint head is secured to the metacarpal bone by means of the screw described above.

When the joint members are in the straightened-out position that is, when the holes 3 and 24 are aligned with each other, there is a substantial play between the insides 27, 28 of the shanks 20, 21 and the areas 8, 11 of the flattened lateral faces of the joint head. The socket therefore is allowed to perform a limited angular motion in the plane of the palm. Said angular motion will cause a sliding displacement of the hemispherical knobs 25, 26 of the shanks 20, 21 in their respective grooves. Owing to the camber of the bottom line of the groove (FIG. 4), no appreciable play between the knobs and the bottoms of the grooves is required in order to allow said sliding displacement. If the joint is regarded from the back-of-the-hand or knuckle side (from the right in FIG. 1), an angular displacement of the socket towards the right in the palm plane (that is, away from the spectator of FIG. 1) will cause the knob engaging the groove 14 visible in FIG. 1 to move away from the base face 2 of the joint head and, owing to the oblique direction of the groove 14, at the same time to move towards the right of FIG. 1, that is, towards the back-of-the-hand or knuckle side of the joint head. The knob engaging the groove of the other side of the joint head performs a movement in the opposite direction (towards the base face 2 and towards the left of FIG. 1). In this way, the socket 29 is caused to perform a rotation about the axis of the hole 24, said rotation being clockwise seen from the base face 2. In a corresponding way, an angular displacement of the socket towards the left (as seen from the knuckle) in the plane of the palm will cause a counterclockwise rotation of the socket as seen from the base face of the joint head.

When the socket is swung towards the palm side from the straightened-out position above referred to, the play between the shanks 20, 21 and the flattened lateral faces of the joint head will decrease gradually as the shanks move across the diverging sectors 7, 10 of said flattened faces. When the angular displacement of the shanks has proceeded so far as to make them encounter the areas 6, 9, the distance between which is less than the distance between the shanks 20, 21 only by the amount required to allow the shanks to slide across said areas, the shanks and, consequently, the entire socket and the phalanx to which it is attached are blocked against lateral angular displacement. In the embodiment of FIGS. 1 to 4, the position of the boundary between the converging sectors 7, 10 and the parallel areas 6, 9 provides a complete blocking of lateral angular movement as soon as the socket has been rotated about 45° towards the palm side from the straightened-out position.

The actions above described closely correspond to those provided by the natural joint. This is important for the practical usefulness of the finger fitted with the prosthetic joint.

Figure 22:
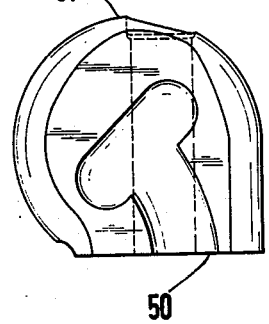
FIG. 22 is a side view, an a smaller scale than FIG. 1, of a modified form of the prosthetic joint head of FIGS. 1 to 4.

The details of the joint design can be varied in many ways. FIG. 22 illustrates a joint head having, compared to the joint head of FIG. 1, an increased ratio of the axial length (that is, the distance from the base face 50 to the crown 51 of the joint head) to the diameter of the spherical slide face. Moreover, the geometrical centre of the spherical slide face has been somewhat displaced towards the palm side of the joint head (the left side in the figure).

The prosthetic interphalangeal joint shown in FIGS. 13 to 16 comprises a joint head 30 and a socket 31. The joint head 30 has a flat base face 32 and a slide face composed of two symmetrical halves 33, 34 each of which forms part of a spherical surface having its centre at E and F, respectively. Moreover, the joint head has a pair of opposed, plane lateral faces 35, 36 extending at right angles to the straight line E - F joining the centres of the spherical surfaces. Each of said plane lateral faces 35, 36 is limited at one side by a shoulder 37, 38, respectively. Said shoulders are facing away from the knuckle side of the joint head (the left side in FIG. 16). Each of said plane faces 35, 36 is provided with a substantially straight groove 39, 40, respectively, extending at right angles to the base face 32 and having an open end forming an indentation in the edge of the base face. The grooves have a semicircular cross-sectional shape and are closed at the end remote from the base face by a spherically rounded end wall merging into the hemicylindrical wall of the groove. The geometrical centres of said spherical surfaces are located on the extension of the line E-F joining the centres of the spherical slide faces 33, 34.

The socket 31 is an U-shaped member having a yoke portion 41 and a pair of parallel shanks 42, 43 each of which is provided at its free extremity with a projection or knob 44, 45 respectively, said knobs being directed towards each other. The yoke portion 41 has the shape of a bowl the inside of which forms a slide face having the same shape as the slide face of the joint head. Thus, it consists of two symmetrical halves each of which forms part of a spherical surface. The straight line joining the centres of said pair of spherical surfaces coincides with the line joining the geometrical centres of the spherical surfaces of the knobs 44, 45. The spherically rounded end walls of the grooves 39, 40 serve as stops for the hemispherical knobs 44, 45 and also may serve as bearings for said knobs.

The joint head and the socket are each provided with a through hole 46, 47, respectively, for receiving a screw or pin by means of which the component is attached to the phalanx. First, the socket is mounted on the outer phalanx. Next, the joint head is put together with the socket by the insertion of the knobs of the socket into the grooves of the joint head. Finally, the joint head is secured to the inner phalanx.

In the joint models represented in FIGS. 13 to 21, there is a sharp boundary between the two spherical surfaces of the slide face of the joint head as well as between the two spherical surfaces of the slide face of the socket. In practice, each of said sharp boundaries is preferably replaced by a softly rounded transition between the spherical surfaces.

I claim:
1. A prosthetic joint comprising a first and a second joint member angularly movable with respect to each other, each of said members being arranged to be attached to one of a pair of skeletal bones, in which said first joint member is a joint head having a base face for resting on a supporting surface provided on one of the skeletal bones, a convex slide face shaped as a part of a surface of revolution having an axis extending through the joint head at a distance from said flat face, and a pair of opposed, flattened lateral guide faces provided each with a groove extending transversely of said base face and said axis of revolution, each of said grooves extending from an open end cutting into said base face to a closed end remote from said base face, said closed end having a spherically rounded, concave end wall, and in which said second joint member is a socket member comprising a bowl-shaped part having an outer top face for resting on a supporting surface provided on the other one of the pair of skeletal bones, a concave inner slide face forming part of a surface of revolution having a shape corresponding to the shape of the convex slide face of the joint head, stem portions attached to said bowl-shaped part and arranged to engage said opposed guide faces, and a pair of essentially hemispherical knobs supported by said stem portions, each of said knobs engaging one of said grooves into which it is admitted through the aforesaid open end of the groove.

2. A prosthetic joint as claimed in claim 1 in which said stem portions form a pair of shanks straddling said joint head.

3. A prosthetic joint as claimed in claim 2 for connecting a metacarpal bone to a phalangeal bone, in which the slide face of the joint head forms part of a sphere the centre of which is located within the joint head and has such a position as to be at least approximately in line with the axis of the skeletal bone for engaging the base face of the joint head, and that each of said grooves comprises a straight portion extending from said closed end and having a rounded cross-sectional shape, both of said straight groove portions being parallel to one and the same plane forming an angle with said axis.

4. a prosthetic joint as claimed in claim 3 in which said straight portion of the groove is terminated at the other end as well by a spherically rounded, concave end wall.

5. A prosthetic joint as claimed in claim 4 in which the distance from said last-mentioned end wall to the base face is less than the radius of the spherical surface of said end wall.

6. A prosthetic joint as claimed in claim 3, in which the bottom of said straight portion of the groove has a camber lengthwise of said straight portion.

7. A prosthetic joint as claimed in claim 6 in which the centre of curvature of said camber coincides with the centre of curvature of the slide face of the joint head.

8. A prosthetic joint as claimed in claim 3, in which the centre of curvature of the concave slide face of the socket member is located on the straight line joining the centres of said hemispherical knobs.

9. A prosthetic joint as claimed in claim 3 in which the centres of curvature of the spherically rounded walls of the ends of the straight groove portions remote from said base face of the joint head are at a larger distance from said base face than the centre of curvature of the spherical slide face of the joint head.

10. A prosthetic joint as claimed in claim 3, in which said plane forms an oblique angle with said axis.

11. A prosthetic joint as claimed in claim 10 in which said plane forms an angle of 45° with said axis.

12. A prosthetic joint as claimed in claim 10 in which the joint head has a palm side and a knuckle side and in which the inclination of each of said straight groove portions is such that a displacement along said groove portion from the end adjacent to said flat face towards the other end is concomitant with a displacement away from the palm side of the joint head.

13. A prosthetic joint as claimed in claim 3 in which each of the pair of grooves comprises, in addition to the straight portion, a second portion extending between a gap in the side wall of said straight portion and said open end of the groove.

14. A prosthetic joint as claimed in claim 3 in which the flat face of the joint member arranged to be attached to the metacarpal bone is essentially plane.

15. A prosthetic joint as claimed in claim 3, in which the distance between the areas of said lateral guide faces which are straddled by said shanks when said shanks are at right angles to the centre axis of the skeletal bone to which the joint head is to be attached is essentially equal to the spacing of said shanks, whereby the joint elements in said relative position are prevented from relative angular displacement in a plane extending through both of said shanks, and in which said lateral guide faces also include areas the distance between which is less than the one of said first-mentioned areas, said second-mentioned areas being connected to the respective first-mentioned areas by a pair of converging sectors of said lateral guide faces.

16. A prosthetic joint as claimed in claim 15 in which the areas of said lateral guide faces which are at a distance from each other essentially equal to the space between the shanks cover a field corresponding to a range of angular displacement of the shanks between the angles of 45° and 90° to the centre axis of the skeleton bone to which the joint head is to be attached.

17. A prosthetic joint as claimed in claim 2 in which the lateral guide faces are plane and parallel and spaced at a distance essentially equal to the space separating the shanks.

18. A prosthetic joint as claimed in claim 1 in which each of said first and second joint members is provided with a through hole for a retaining screw arranged to engage internal threads provided in the corresponding skeletal bone or in a fixture secured to the corresponding skeletal bone.

* * * * *